US008519019B2

(12) United States Patent
Dhaler et al.

(10) Patent No.: US 8,519,019 B2
(45) Date of Patent: Aug. 27, 2013

(54) DENTAL COMPOSITION BASED ON A COLLOIDAL SILICA SOLUTION IN A CONTINUOUS SILICON PHASE

(75) Inventors: Didier Dhaler, Tassin (FR); Jean-Marc Frances, Meyzieu (FR)

(73) Assignee: Bluestar Silicones France SAS, Lyons (FR)

( * ) Notice: Subject to any disclaimer, the term of this patent is extended or adjusted under 35 U.S.C. 154(b) by 1167 days.

(21) Appl. No.: 10/498,551

(22) PCT Filed: Dec. 17, 2002

(86) PCT No.: PCT/FR02/04392
§ 371 (c)(1),
(2), (4) Date: Feb. 22, 2005

(87) PCT Pub. No.: WO03/051317
PCT Pub. Date: Jun. 26, 2003

(65) Prior Publication Data
US 2005/0119367 A1 Jun. 2, 2005

(30) Foreign Application Priority Data
Dec. 18, 2001 (FR) ........................ 0116404

(51) Int. Cl.
C08G 59/68 (2006.01)
C07D 303/02 (2006.01)
A61K 6/087 (2006.01)
A61K 6/093 (2006.01)

(52) U.S. Cl.
USPC ............ 523/115; 523/113; 522/25; 522/31; 522/170; 522/172; 522/908; 433/228.1

(58) Field of Classification Search
USPC ............... 523/115, 116, 118, 113; 522/148, 522/25, 31, 170, 172, 908; 433/228.1
See application file for complete search history.

(56) References Cited

U.S. PATENT DOCUMENTS

| 3,462,374 | A  | * | 8/1969  | Klosak ............................ 516/81 |
| 4,455,205 | A  |   | 6/1984  | Olson et al. |
| 4,781,940 | A  | * | 11/1988 | Denton, Jr. ................... 427/2.14 |
| 5,321,075 | A  | * | 6/1994  | Liles ............................. 524/837 |
| 5,990,195 | A  | * | 11/1999 | Arita ............................. 523/116 |
| 6,096,903 | A  | * | 8/2000  | Moszner et al. .............. 549/214 |
| 6,245,828 | B1 | * | 6/2001  | Weinmann et al. ........... 522/148 |
| 6,302,926 | B1 | * | 10/2001 | Anselmann et al. ......... 23/313 R |
| 6,362,251 | B1 | * | 3/2002  | Alkemper et al. ............ 523/116 |
| 6,417,246 | B1 | * | 7/2002  | Jia et al. ....................... 523/113 |
| 6,620,861 | B1 | * | 9/2003  | Nakatuka et al. ............. 523/212 |
| 6,747,071 | B1 | * | 6/2004  | Frances ......................... 522/148 |
| 2002/0035199 | A1 | * | 3/2002  | Breunig et al. ............... 524/588 |
| 2002/0156152 | A1 | * | 10/2002 | Zhang et al. .................. 523/115 |
| 2003/0035899 | A1 | * | 2/2003  | Klettke et al. ................ 427/387 |
| 2005/0123762 | A1 | * | 6/2005  | Ori et al. ...................... 428/407 |

FOREIGN PATENT DOCUMENTS

| EP | 0 562 897 | 9/1993 |
| JP | 11 100305 | 7/1999 |
| WO | 00 19966  | 4/2000 |
| WO | 00 19967  | 4/2000 |

OTHER PUBLICATIONS

MSDS Nalco 2329; Nalco Company, Jan. 11, 2008.*

* cited by examiner

Primary Examiner — Michael Pepitone
(74) Attorney, Agent, or Firm — Dentons US LLP

(57) ABSTRACT

The invention relates to dental compositions which can be used to produce dental prostheses and for dental restoration. The inventive compositions comprise: (1) a concentrated silica solution comprising colloidal amorphous silica particles in at least one continuous silicon phase, consisting of polymerisable and/or crosslinkable silicon polymer and/or oligomer; (2) at least one photosensitiser; and (3) a cationic initiator which is selected from among those comprising a cationic entity selected from onium salts having formula (1): $[(R^1)n\text{-}A\text{-}(R^2)m]^+$ 22 Claims, No Drawings

DENTAL COMPOSITION BASED ON A COLLOIDAL SILICA SOLUTION IN A CONTINUOUS SILICON PHASE

The field of the invention is that of dental compositions. More specifically, the dental compositions developed in the context of the present invention can be used for the preparation of dental prostheses and for dental restoration.

To date, resins based on photopolymerizable acrylates can be used to prepare dental compositions for the preparation of dental prostheses or of dental restoration materials. However, these ready-to-formulate products exhibit, on use, problems of irritation and potential problems of toxicity.

In addition, these products exhibit the major disadvantage of resulting in a significant shrinkage in volume when they are polymerized, which makes it complex and difficult to use them in the preparation of dental prostheses or of dental restoration materials. In particular, problems of bonding due to the shrinkage in volume or to the lack of adhesion of the polymers used are observed.

To overcome these disadvantages, the Applicant Company has already provided dental silicone compositions with improved qualities, in particular as regards the very marked reduction in the phenomenon of shrinkage of the dental compositions used for the preparation of dental prostheses or of dental restoration materials. On this subject, Application WO 00/19997 provides dental compositions based on:

a crosslinkable or polymerizable silicone oligomer or polymer comprising:
at least one unit of formula:

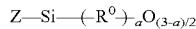

in which:
a=0, 1 or 2,
$R^0$, which are identical or different, represent an alkyl, cycloalkyl, aryl, vinyl, hydrogen or alkoxy radical, preferably a lower $C_1$-$C_6$ alkyl,
Z, which are identical or different, is an organic substituent comprising at least one epoxy and/or alkenyl ether and/or oxetane and/or dioxolane and/or carbonate reactive functional group and preferably Z being an organic substituent comprising at least one epoxy and/or dioxolane reactive functional group,
and at least two silicon atoms, an effective amount of at least one initiator of borate type,
at least one aromatic hydrocarbonaceous photosensitizer comprising one or more substituted or unsubstituted aromatic rings having a residual absorption of the light between 200 and 500 nm,
and at least one dental filler present in a proportion of at least 10% by weight with respect to the total weight of the composition.

However, no indication is given in this prior art for the development of dental compositions based on colloidal silica and on crosslinkable and/or polymerizable silicone for preparing dental materials with a reinforced hardness, in particular with respect to salivary abrasion. In addition, these dental compositions have to exhibit a low opacity in order to facilitate a polymerization/crosslinking thereof.

The main object of the present invention is thus to provide novel dental compositions exhibiting, after crosslinking/polymerization, (i) a hardness of at least 30 HV (Vicker's hardness) for a load of 500 grams, preferably of at least 40 HV, and (ii) a degree of opacity which makes possible homogeneous and simultaneous crosslinking and/or polymerization of said composition over a thickness of at least 3 mm in less than one minute under UV radiation of visible wavelengths (200 to 500 nm, preferably greater than 400 nm).

Other essential objects of the invention consist in providing a silicone dental composition which offers a technical solution advantageous with regard to the cost, ease of use (in particular packaging, for example in the "monocomponent" form) and high stability on storage. Furthermore, these compositions are nontoxic and virtually nonirritating.

The polymerizable and/or crosslinkable dental composition according to the invention comprises:

a concentrated silica solution (1) composed of 15 to 80% of colloidal particles of amorphous silica in at least one continuous silicone phase composed of crosslinkable and/or polymerizable silicone oligomer and/or polymer which is liquid at ambient temperature or heat-fusible at a temperature below 100° C., the silicone oligomer and/or polymer comprising:
at least one unit of formula (FS):

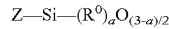

in which:
a=0, 1 or 2,
$R^0$, which are identical or different, represent an alkyl, cycloalkyl, aryl, vinyl, hydrogen, hydroxyl or alkoxy radical, preferably a lower $C_1$-$C_6$ alkyl,
Z, which are identical or different, is an organic substituent comprising at least one epoxy and/or alkenyl ether and/or oxetane and/or dioxolane and/or carbonate reactive functional group,
and at least two silicon atoms,
at least one aromatic hydrocarbonaceous photosensitizer (2) comprising one or more substituted or unsubstituted aromatic rings having a residual absorption of the light between 200 and 500 nm,
and at least one photoinitiator (3), the cationic entity of which of the initiator is selected from the onium salts of formula (I):

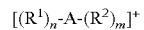            (I)

in which formula,
A represents an element from Groups 15 to 17 [Chem. & Eng. News, Vol. 63, No. 5, 26, of 4 Feb. 1985], such as, for example: I, S, Se, P or N,
$R^1$ represents a $C_6$-$C_{20}$ carbocyclic or heterocyclic aryl radical, it being possible for said heterocyclic radical to comprise, as heteroelements, nitrogen or sulfur,
$R^2$ represents $R^1$ or a linear or branched $C_1$-$C_{30}$ alkyl or alkenyl radical; said $R^1$ and $R^2$ radicals optionally being substituted by a $C_1$-$C_{25}$ alkoxy, $C_1$-$C_{25}$ alkyl, nitro, chloro, bromo, cyano, carboxyl, ester or mercapto group,
n is an integer ranging from 1 to v+1, v being the valency of the element A,
m is an integer ranging from 0 to v−1 with n+m=v+1.

The polymerizable and/or crosslinkable dental composition according to the invention comprises:
(1), a concentrated silica solution composed of 15 to 80% of colloidal particles of amorphous silica with a mean diameter between $10^{-6}$ and $10^{-9}$ in at least one continuous silicone phase composed of crosslinkable and/or polymerizable silicone oligomer and/or polymer which is liquid at ambient temperature or heat-fusible at a temperature below 100° C., the silicone oligomer and/or polymer comprising:
at least one unit of formula (FS):

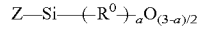

in which:
a 0, 1 or 2,
$R^0$, which are identical or different, represent an alkyl, cycloalkyl, aryl, vinyl, hydrogen, hydroxyl or alkoxy radical, preferably a lower $C_1$-$C_6$ alkyl,
Z, which are identical or different, is an organic substituent comprising at least one epoxy and/or alkenyl ether and/or oxetane and/or dioxolane and/or carbonate reactive functional group,
and at least two silicon atoms,
(2) at least one aromatic hydrocarbonaceous photosensitizer comprising one or more substituted or unsubstituted aromatic rings having a residual absorption of the light between 200 and 500 nm,
(3) and an effective amount of at least one cationic initiator chosen from those for which the cationic entity is selected from the onium salts of formula (I):

$[(R^1)_n\text{-}A\text{-}(R^2)_m]^+$ (I)

in which formula:
A represents an element from Groups 15 to 17 such as for example: I, S, Se, P or N,
$R^1$ represents a $C_6$-$C_{20}$ carbocyclic or heterocyclic aryl radical, it being possible for said heterocyclic radical to comprise, as heteroelements, nitrogen or sulfur,
$R^2$ represents $R^1$ or a linear or branched $C_1$-$C_{30}$ alkyl or alkenyl radical; said $R^1$ and $R^2$ radicals optionally being substituted by a $C_1$-$C_{25}$ alkoxy, $C_1$-$C_{25}$ alkyl, nitro, chloro, bromo, cyano, carboxyl, ester or mercapto group,
n is an integer ranging from 1 to v+1, v being the valency of the element A,
m is an integer ranging from 0 to v−1 with n+m=v+1.

In general, the dental composition can be polymerized and/or crosslinked under activation (i) photochemically and/or (ii) photochemically and thermally.

Photochemical activation is carried out under UV radiation. More particularly, use is made of UV radiation with a wavelength of the order of 200 to 500 nm for the preparation of dental prostheses and UV-visible radiation with a wavelength of greater than 400 nm for the preparation of restoration materials. A wavelength of greater than 400 nm makes possible crosslinking and/or polymerization in an oral environment.

The novel dental composition based on amorphous silica dispersed in a silicone polymer or oligomer (1) exhibits the advantage of being transparent to UV-visible light and thus the use thereof makes it possible to obtain very thick materials which can be photocrosslinked in a very short time.

The Z reactive functional groups of the silicone polymer or oligomer (1) can be highly varied. However, particularly advantageous dental compositions are obtained when the silicone oligomer or polymer (1) comprises at least one (FS) unit in which Z represents an organic substituent Z1 comprising at least one epoxy and/or dioxolane reactive functional group and preferably at least one epoxy reactive functional group.

According to two advantageous alternatives of the present invention, the silicone oligomer or polymer (1) with at least one epoxy and/or dioxolane reactive functional group Z1 and preferably at least one epoxy reactive functional group can:
(i) either comprise only this/these type(s) of reactive functional group(s) Z1,
(ii) or comprise other reactive functional groups Z, such as the alkenyl ether, oxetane and/or carbonate reactive functional groups Z2.

In the case of the first alternative (i), the dental composition can also comprise other silicone oligomers and/or polymers comprising other reactive functional groups Z2, such as alkenyl ether, oxetane and/or carbonate functional groups, and optionally reactive functional groups Z1.

As examples of reactive functional groups Z, the latter can be chosen in particular from the following radicals:

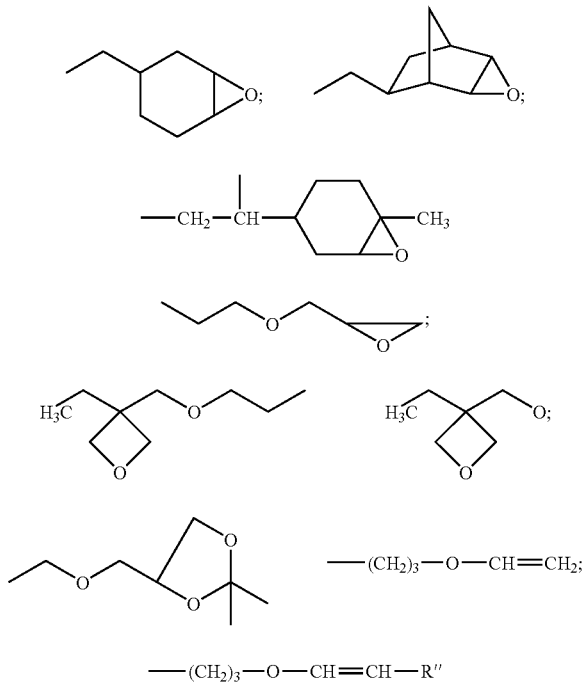

with R″ representing a linear or branched $C_1$-$C_6$ alkyl radical.

According to a second advantageous alternative form of the present invention, the silicone polymer or oligomer is composed of at least one silicone of following mean formula:

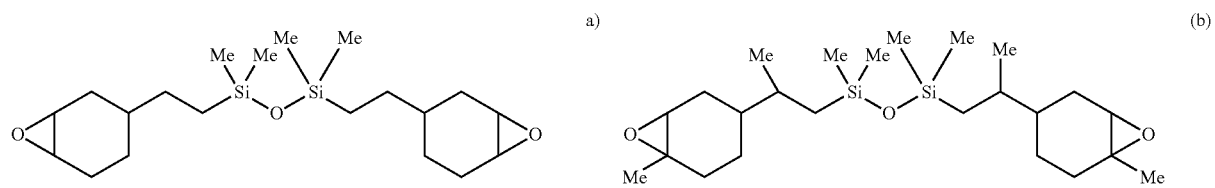

c) 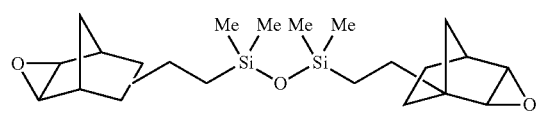
d) 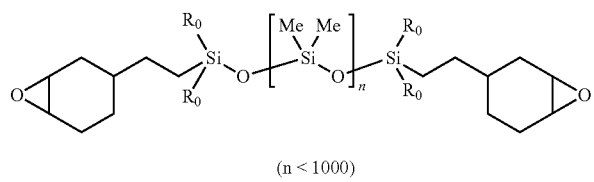
(n < 1000)
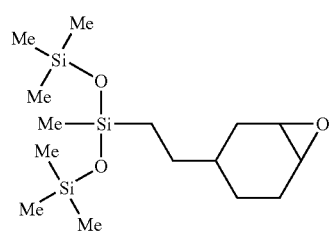
f) 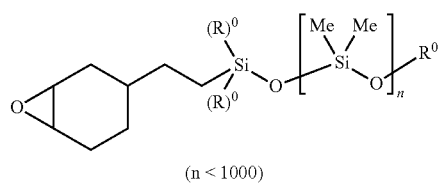
(n < 1000)
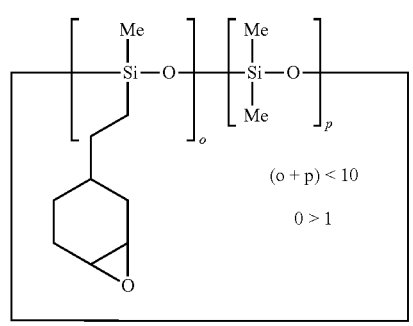
(o + p) < 10
o > 1
g) 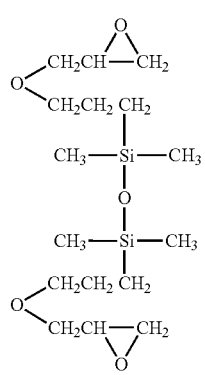
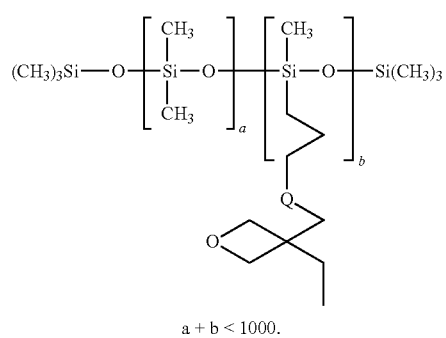
a + b < 1000.
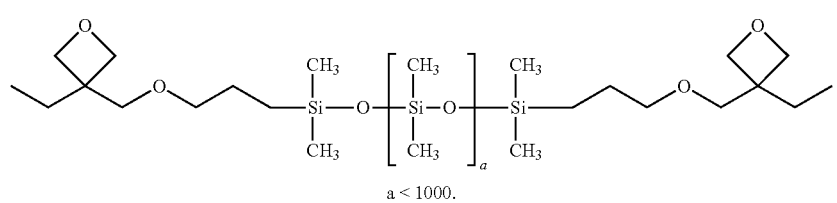
a < 1000.
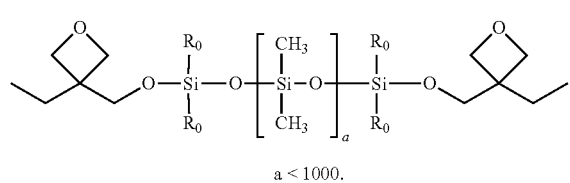
a < 1000.

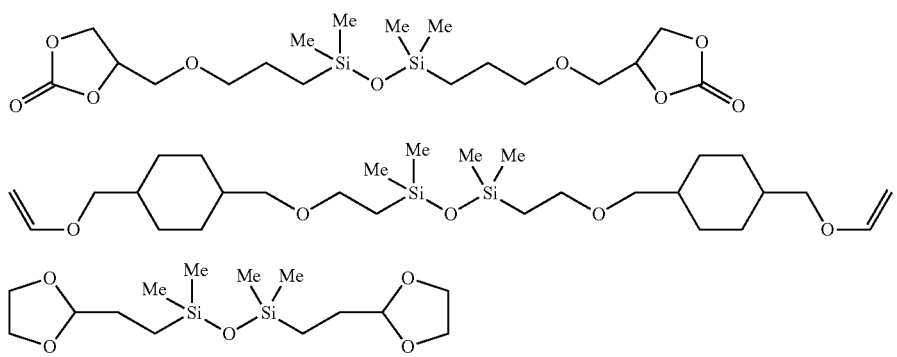

Various procedures can be employed to prepare the solution of amorphous silica in a continuous silicone phase; in the context of the invention, solutions of silica of dispersion type will preferably be employed.

To this end, the silica used can have various sources: precipitated silica, fumed silica, silica aerogels, silica sol and/or natural silica.

According to a preferred form of the invention, the amorphous silica predominantly or entirely present in the silicone phase results from silica sols and more particularly from silica organosols; a general description of silica sols is given in the document U.S. Pat. No. 2,801,185 and "The Colloid Chemistry of Silica and Silicates" (Ralph K. Iler, Cornell University Press, 1955, see in particular pages 120-121). In this case, the process for the preparation of the dispersion of silica in the continuous silicone phase is generally (i) to mix the silica organosol with the silicone (1), the organosol being selected such that its solvent is compatible with said silicone, then (ii) to remove [for example under reduced pressure and/or heating] the solvent and (iii) to thus obtain a dispersion of amorphous silica in a continuous silicone phase.

Mention may be made, as examples of commercial silica organosols, of those from Clariant, Fuso Chemicals, Nalco, Degussa-Huls and Dupont Chemicals.

Mention will be made, for Clariant, of the following products: Highlink® OG 1-32, Highlink® OG4-53, Highlink® OG8-32, Highlink® OG 401-31, Highlink® OG401-51, Highlink® OG502-30, Highlink® OG502-31 and Highlink® OG600-51.

According to a preferred alternative form of the invention, the anionic entity of the cationic initiator is a borate of formula $[BX_aR_b]^-$ in which:

a and b are integers ranging, for a, from 0 to 3 and, for b, from 1 to 4, with a+b=4, the symbols X represent:
  a halogen atom (chlorine, fluorine) with a=0 to 3,
  an OH functional group with a=0 to 2, the symbols R are identical or different and represent:
  a phenyl radical substituted by at least one electron-withdrawing group, such as, for example, $OCF_3$, $CF_3$, $NO_2$ or CN, and/or by at least 2 halogen atoms (very particularly fluorine), this being the case when the cationic entity is an onium of an element from Groups 15 to 17,
  a phenyl radical substituted by at least one electron-withdrawing element or group, in particular a halogen atom (very particularly fluorine), $CF_3$, $OCF_3$, $NO_2$ or CN, this being the case when the cationic entity is an organometallic complex of an element from, Groups 4 to 10,
  an aryl radical comprising at least two aromatic nuclei, such as, for example, biphenyl or naphthyl, which is optionally substituted by at least one electron-withdrawing element or group, in particular a halogen atom (very particularly fluorine), $OCF_3$, $CF_3$, $NO_2$ or CN, whatever the cationic entity.

As preferred alternative form of the invention for the types of the borate anionic entity, those which are very particularly suitable are as follows:

| | |
|---|---|
| 1': | $[B(C_6F_5)_4]^-$ |
| 2': | $[(C_6F_5)_2BF_2]^-$ |
| 3': | $[B(C_6H_4CF_3)_4]^-$ |
| 4': | $[B(C_6F_4OCF_3)_4]^-$ |
| 5': | $[B(C_6H_3(CF_3)_2)_4]^-$ |
| 6': | $[B(C_6H_3F_2)_4]^-$ |
| 7': | $[C_6F_5BF_3]^-$ |

According to another preferred alternative form of the invention, the onium salts which can be used are those disclosed in particular in Patents U.S. Pat. Nos. 4,026,705, 4,032,673, 4,069,056, 4,136,102 and 4,173,476. Among these, preference will very particularly be given to the following cations:

| | |
|---|---|
| $[CH_3\text{-}\Phi\text{-}I\text{-}\Phi\text{-}CH_2CH(CH_3)_2]^+$ | $[C_8H_{17}\text{—}O\text{-}\Phi\text{-}I\text{-}\Phi]^+$ |
| $[(\Phi\text{-}CH_3)_2 I]^+ [C_{12}H_{25}\text{-}\Phi\text{-}I\text{-}\Phi]^+$ | $[(C_8H_{17}\text{—}O\text{-}\Phi)_2 I]^+$ |
| $[(C_8H_{17}\text{—}O\text{-}\Phi\text{-}I\text{-}\Phi)]^+$ | $[(\Phi)_3S]^+$ |
| $[(\Phi)_2\text{-}S\text{-}\Phi\text{-}O\text{—}C_8H_{17}]^+$ | $[CH_3\text{-}\Phi\text{-}I\text{-}\Phi\text{-}CH(CH_3)_2]^+$ |
| $[\Phi\text{-}S\text{-}\Phi\text{-}S\text{-}(\Phi)_2]^+$ | $[C_{12}H_{25}\text{-}\Phi)_2I]^+$ |
| and $[CH_3\text{-}\Phi\text{-}I\text{-}\Phi\text{-}OC_2H_5]^+$. | |

In agreement with these preferred alternative forms, mention may be made, as examples of initiators of the onium borate type, of the following products:

| | |
|---|---|
| $[CH_3\text{-}\Phi\text{-}I\text{-}\Phi\text{-}CH_2CH(CH_3)_2]^+$ | $[B(C_6F_5)_4]^-$ |
| $[(C_8H_{17})\text{—}O\text{-}\Phi\text{-}I\text{-}\Phi]^+ [B(C_6F_5)_4]^-$ | $[C_{12}H_{25}\text{-}\Phi\text{-}I\text{-}\Phi\text{-}CH(CH_3)_2]^+$ $[B(C_6F_5)_4]^-$ |
| $[(C_8H_{17})\text{—}O\text{-}\Phi)_2I]^+ [B(C_6F_5)_4]^-$ | $[CH_3\text{-}\Phi\text{-}I\text{-}\Phi\text{-}CH(CH_3)_2]^+ [B(C_6F_5)_4]^-$ |
| $[(C_8H_{17})\text{—}O\text{-}\Phi\text{-}I\text{-}\Phi]^+ [B(C_6F_5)_4]^-$ | $[(\Phi)_3S]^+ [B(C_6F_5)_4]^-$ |
| $[(\Phi)_2S\text{-}\Phi\text{-}O\text{-}C_8H_{17}]^+$ $[B(C_6H_4CF_3)_4]^-$ | $[(C_{12}H_{25}\text{-}\Phi)_2I]^+ [B(C_6F_5)_4]^-$ |
| $[(\Phi)_3S]^+ [B(C_6F_4OCF_3)_4]^-$ and $[(\Phi\text{-}CH_3)_2 I]^+$, $[B(C_6F_4OCF_3)_4]^-$. | $[(\Phi\text{-}CH_3)_2I]^+ [B(C_6F_5)_4]^-$ |

The photosensitizer present in the dental composition according to the invention can be highly varied in nature. In the context of the invention, the photosensitizer can be chosen from the photosensitizers disclosed in Application WO 00/19967 and in particular those of "formulae (IV) to (XXII)" and more particularly those-corresponding to the formulae (IV), (VII) and (VIII). Their selection is made according to the same criteria as those indicated in this application.

Within the dental composition, the percentage of filler(s) by weight with respect to the total weight of the dental composition at least 10%, preferably at least 15%, and at most 90%.

The filler of the dental composition can be composed solely of amorphous silica resulting from the concentrated dispersion of silica in the silicone phase. However, additional fillers may be used. These fillers are chosen according to the final use of the dental composition: they modify important properties, such as the appearance, the penetration of UV radiation and the mechanical and physical properties of the material obtained after crosslinking and/or polymerizing the dental composition.

Use may be made, as reinforcing filler, of treated or untreated pyrogenic silica fillers, amorphous silica fillers [in addition to those present in the dispersion (1)], quartz, glasses or nonvitreous fillers based-on zirconium, barium, calcium, fluorine, aluminum, titanium or zinc oxides, borosilicates, aluminosilicates, talc, spherosils, ytterbium trifluoride, or fillers based on polymers in the milled powder form, such as poly(methyl methacrylate)s, which may be inert or functionalized, polyepoxides or polycarbonates.

Mention will be made, as examples, of:
  inert fillers based on poly(methyl methacrylate) Luxaself from UGL, which can be used in the dental field and which are pigmented pink,
  fillers formed from fumed silica which has been treated with hexamethyldisilazane with a specific surface of 200 m$^2$/g,
  untreated fumed silica fillers ("Aerosil" AE200, sold by Degussa).

According to an advantageous alternative form of the invention, the fillers and in particular the silica fillers are treated before use at 120° C. with an amount of less than 10% w/w of silicone comprising at least one unit with the formula below:

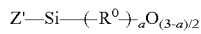

such that Z' has the same definition as Z
a=0, 1, 2 or 3
and with at least one silicon atom.

In this case of treatment of silicon filler or fillers, in particular silica, with this type of silicone, the material obtained after crosslinking exhibits a mechanical strength, a modulus of elasticity and a compressive strength which is markedly improved.

In addition to the reinforcing fillers, pigments can be used to color the dental composition according to the use envisaged and ethnic groups.

For example, red pigments are used in the presence of microfibers for dental compositions used for the preparation of dental prostheses in order to stimulate blood vessels.

Pigments based on metal oxides (iron and/or titanium and/or aluminum and/or zirconium oxides, and the like) are also employed for dental compositions used for the preparation of restoration material, in order to obtain a crosslinked material with an ivory color.

Other additives can be incorporated in the dental compositions according to the invention, for example biocides, stabilizers, flavoring agents, plasticizers and adhesion promoters.

Use will advantageously be made, among the additives which can be envisaged, of crosslinkable and/or polymerizable coreactants of organic type. These coreactants are liquid at ambient temperature or heat-fusible at a temperature below 100° C., and each coreactant comprises at least two reactive functional groups, such as oxetane-alkoxy, oxetane-hydroxyl, oxetane-alkoxysilyl, carboxyl-oxetane, oxetane-oxetane, alkenyl ether-hydroxyl, alkenyl ether-alkoxysilyl, epoxy-alkoxy, epoxy-alkoxysilyl, dioxolane-dioxolane-alcohol, and the like.

The dental compositions according to the invention can be used in numerous dental applications and in particular in the field of dental prostheses, in the field of dental restoration and in the field of temporary teeth.

The dental composition according to the invention is preferably provided in the form of a single product comprising the various components ("monocomponent"), which facilitates the use thereof, in particular in the field of dental prostheses. Optionally, the stability of this product can be ensured by organic derivatives comprising amine functional groups, according to the teaching of the document WO 98/07798.

In the field of dental prostheses, the product in the "monocomponent" form can be deposited using a syringe directly on the plaster model or in a core. It is then polymerized (polymerization by possible successive layers) using a UV lamp (visible light spectrum 200-500 nm).

In general, it is possible to prepare in 10 to 15 minutes a lasting and attractive dental prosthesis.

It should be noted that the products obtained from the dental composition according to the invention are nonporous. Thus, after optional polishing using a felt brush, for example, the surface of the dental prostheses obtained is smooth and bright and thus does not require the use of varnish.

The applications in the field of dental prostheses are essentially those of the joined prosthesis, which can be divided into two types:
  full prosthesis in the case of a completely toothless patient,
  partial prosthesis due to the absence of several teeth, which is reflected either by a provisional prosthesis or by a skeleton brace.

In the field of dental restoration, the dental composition according to the invention can be used as rapid and easy-to-use material for filling the anterior and posterior teeth in different colors (for example, "VITA" colors).

As the dental composition is nontoxic and can be polymerized in thick layers, it is not essential to polymerize the material in successive layers. Generally, a single injection of the dental composition is sufficient.

The preparations for dental prostheses and for restoration materials are produced according to the conventional techniques of the art.

In the case of application of the dental composition to a tooth, either the tooth can be pretreated with a bonding primer or the dental composition can be prepared as a mixture with a bonding primer before use thereof. However, it is not essential to use a bonding primer in using the dental composition according to the invention.

The following examples and tests are given by way of illustration. They make it possible in particular to achieve a better understanding of the invention and to highlight some of its advantages and to illustrate a few of its alternative embodiments.

EXAMPLES AND TESTS

The products used in the compositions of the examples are as follows:
the silicone oligomer comprising an epoxide functionality of formula (A):

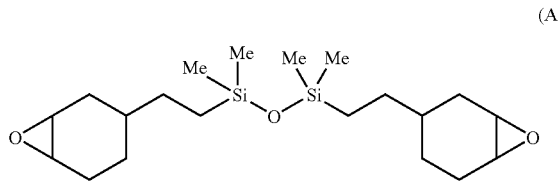

the onium borate initiator (P1):

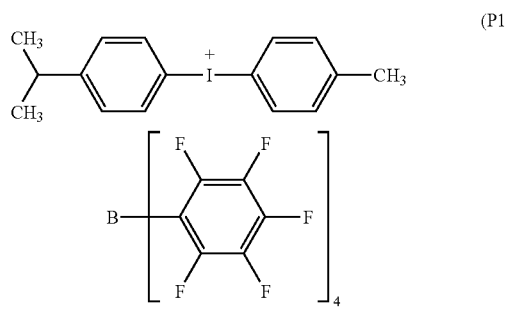

the silica organosol Highlink®OG502-31 from Clariant,
the fumed silica sold under the name OX50 from Degussa,
the photosensitizer (PS1): isopropylthio-xanthone
the commercial stabilizer Tinuvin® 765 from Ciba,
and the filler of amorphous quartz type.

Example 1

Preparation of the Dispersion of Amorphous Silica in a Silicone Phase 15 g of siloxane A stabilized by 90 ppm of Tinuvin® 765 and 50 g of silica organosol in isopropanol are charged to a round-bottomed flask.

After devolatilization of the isopropanol with stirring and under reduced pressure, a dispersion of silica in the siloxane A monomer comprising 47% by weight of silica and with a particle size of less than 40 nm is obtained.

The mean size of the silica particles is 15 nm. The solution is clear and colorless and has a viscosity of 5000 mPa·s.

Example 2

Preparation of a Control Dental Composition

A control composition is obtained by mixing 52.18% by weight of monomer A, 47% by weight of ground quartz (Sifraco C60), 0.8% by weight of initiator P1, 70 ppm of isopropylthioxanthone and 90 ppm of Tinuvun 765.

The photoinitiator P1 and the photosensitizer are in the solid form and are premixed with the monomer A comprising the product Tinuvin 765 with stirring.

The quartz is introduced at the end when the ITX and the photoinitiator have completely dissolved. A dark brown paste is obtained.

After exposure under a UV lamp with a wavelength of greater than 400 nm and with a power of 600 mW/cm$^2$, the composition crosslinks only over a thickness of less than 1 mm through a sheet of polyester with a thickness of 100 microns.

Example 3

Preparation of a Dental Composition According to the Invention

A composition according to the invention is obtained by mixing 99.18% of silica dispersion according to Example 1, 0.8% of initiator P1, 70 ppm of PS1 and 90 ppm of Tinuvin 765.

A clear and colorless solution is obtained by pouring the photosensitizer/photoinitiator mixture into the dispersion obtained in Example 1 with stirring 1 minute.

After exposure under a UV lamp with a wavelength of greater than 400 nm and with a power 600 mW/cm$^2$, the composition is crosslinked over a thickness of at least 3 mm through a sheet of polyester with a thickness of 100 microns in 40 seconds. The hardness is 40 HV (Vickers hardness) under a load of 500 grams.

Example 4

Preparation of a Dental Composition According to the Invention

A composition according to the invention is obtained by mixing 50% of dispersion of example 1, 44.2% of ground quartz SiO$_2$ (particle diameter such that the mean distribution is 3.5±1 microns), 5% of YbF$_3$, 0.8% of initiator P1, 100 ppm of sensitizer PS1 and 90 ppm of Tinuvin 765, the last three being present in solution in the monomer A (30% of P1 in the monomer A).

A translucent composition is obtained by mixing with stirring for 15 minutes.

This composition crosslinks over a thickness of at least 3 mm under a UV lamp (wavelength of greater than 400 nm and power 600 mW/cm$^2$) through a sheet of polyester with a thickness of 100 microns over 40 seconds. The hardness is 60 HV (Vickers hardness) under a load of 500 grams.

Example 5

Preparation of a Dental Composition According to the Invention

A composition according to the invention is obtained by mixing 50% of dispersion of example 1, 24.2% of ground quartz SiO$_2$ (particle diameter such that the mean distribution is 3.5±1 micron), 20% of fumed silica, 5% of YbF$_3$, 0.8% of initiator P1, 100 ppm of sensitizer PS1 and 90 ppm of Tinuvin 765, the last three being present in solution in the monomer A (30% of P1 in the monomer A).

A virtually transparent composition is obtained by mixing with stirring for 15 minutes.

This composition crosslinks over a thickness of at least 3 mm under a UV lamp (wavelength of greater than 400 nm and power of 600 mW/cm$^2$) through a sheet of polyester with a thickness of 100 microns over 40 seconds. The hardness is 70 HV (Vickers hardness) under a load of 500 grams.

The dental materials obtained in examples 3 (= resistance +), 4 (= resistance ++) and 5 (= resistance +++) exhibit a high

What is claimed is:

1. A dental composition comprising:
   (A) a concentrated silica solution comprising 15 to 80% of colloidal particles of amorphous silica in at least one continuous silicone phase, wherein the at least one continuous silicone phase comprises a crosslinkable and/or polymerizable silicone oligomer and/or polymer which is liquid at ambient temperature or heat-fusible at a temperature below 100° C., the silicone oligomer and/or polymer comprising:
      (i) at least one unit of formula (FS):

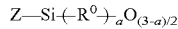

in which:
      a=0, 1 or 2,
      $R^0$, which are identical or different, represent an alkyl, cycloalkyl, aryl, vinyl, hydrogen, hydroxyl or alkoxy radical,
      Z, which are identical or different, is an organic substituent comprising at least one epoxy and/or alkenyl ether and/or oxetane and/or dioxolane and/or carbonate reactive functional group,
      (ii) and at least two silicon atoms,
   (B) at least one aromatic hydrocarbonaceous photosensitizer comprising one or more substituted or unsubstituted aromatic rings having a residual absorption of the light between 200 and 500 nm,
   (C) at least one cationic initiator selected from those for which the cationic entity is selected from the onium salts of formula (I):

$$[(R^1)_n\text{-}A\text{-}(R^2)_m]^+ \qquad (I)$$

in which formula:
      A represents an element from Groups 15 to 17,
      $R^1$ represents a $C_6$-$C_{20}$ carbocyclic or heterocyclic aryl radical, where the heteroelements in said heterocyclic aryl radical are nitrogen or sulfur,
      $R^2$ represents $R^1$ or a linear or branched $C_1$-$C_{30}$ alkyl or alkenyl radical; said $R^1$ and $R^2$ radicals optionally being substituted by a $C_1$-$C_{25}$ alkoxy, $C_1$-$C_{25}$ alkyl, nitro, chloro, bromo, cyano, carboxyl, ester or mercapto group,
      n is an integer ranging from 1 to v+1, v being the valency of the element A,
      m is an integer ranging from 0 to v−1 with n+m=v+1.

2. The dental composition as claimed in claim 1, comprising:
   (A) a concentrated silica solution of comprising 15 to 80% of colloidal particles Of amorphous silica with a mean diameter between $10^{-6}$ m and $10^{-9}$ m in at least one continuous silicone phase of comprising crosslinkable and/or polymerizable silicone oligomer and/or polymer which is liquid at ambient temperature or heat-fusible at a temperature below 100° C., the silicone oligomer and/or polymer comprising:
      (i) at least one unit of formula (FS):

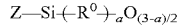

in which:
      a=0, 1 or 2,
      $R^0$, which are identical or different, represent an alkyl, cycloalkyl, aryl, vinyl, hydrogen, hydroxyl or alkoxy radical,
      Z, which are identical or different, is an organic substituent comprising at least one epoxy and/or alkenyl ether and/or oxetane and/or dioxolane and/or carbonate reactive functional group,
      (ii) and at least two silicon atoms,
   (B) at least one aromatic hydrocarbonaceous photosensitizer comprising one or more substituted or unsubstituted aromatic rings having a residual absorption of the light between 200 and 500 nm,
   (C) and an effective amount of at least one cationic initiator selected from those for which the cationic entity is selected from the onium salts of formula (I):

$$[(R^1)_n\text{-}A\text{-}(R^2)_m]^+ \qquad (I)$$

in which formula:
      A represents an element from Groups 15 to 17
      $R^1$ represents a $C_6$-$C_{20}$ carbocyclic or heterocyclic aryl radical, where the heteroelements in said heterocyclic aryl radical are nitrogen or sulfur,
      $R^2$ represents $R^1$ or a linear or branched $C_1$-$C_{30}$ alkyl or alkenyl radical; said $R^1$ and $R^2$ radicals optionally being substituted by a $C_1$-$C_{25}$ alkoxy, $C_1$-$C_{25}$ alkyl, nitro, chloro, bromo, cyano, carboxyl, ester or mercapto group,
      n is an integer ranging from 1 to v+1, v being the valency of the element A,
      m is an integer ranging from 0 to v−1 with n+m=v+1.

3. The dental composition as claimed in claim 1 wherein the anionic entity of the initiator is a borate of formula $[BX_a R_b]^-$ in which:
   a and b are integers ranging, for a, from 0 to 3 and, for b, from 1 to 4, with a+b=4,
   – the symbols X represent:
      a halogen atom (chlorine, fluorine) with a =0 to 3,
      an OH functional group with a=0 to 2,
   the symbols R are identical or different and represent:
      a phenyl radical substituted by at least one electron-withdrawing group, $OCF_3$, $CF_3$, $NO_2$ or CN, and/or by at least 2 halogen atoms, this being the case when the cationic entity is an onium of an element from Groups 15 to 17,
      a phenyl radical substituted by at least one electron-withdrawing element or group, $CF_3$, $OCF_3$, $NO_2$ or CN, this being the case when the cationic entity is an organometallic complex of an element from Groups 4 to 10,
      an aryl radical comprising at least two aromatic nuclei, which is optionally substituted by at least one electron-withdrawing element or group, $OCF_3$, $CF_3$, $NO_2$ or CN, whatever the cationic entity.

4. The composition as claimed in claim 1, wherein Z is an organic substituent Z1 comprising at least one epoxy and/or dioxolane reactive functional group and optionally at least one epoxy reactive functional group.

5. The composition as claimed in claim 1, wherein the oligomer or polymer (1) additionally comprises other reactive functional groups Z such as the alkenyl ether, oxetane and/or carbonate reactive functional groups Z2.

6. The composition as claimed in claim 1, wherein the reactive functional group or groups of Z1 are selected from the following radicals:

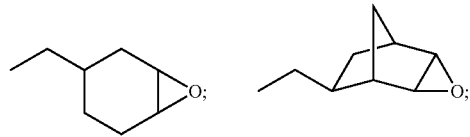

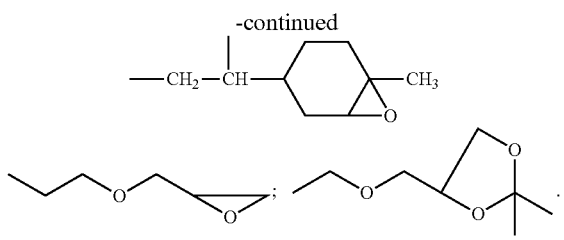

7. The composition as claimed in claim 1, wherein the photoinitiator is selected from the group consisting of:

| | |
|---|---|
| [CH₃-Φ-I-Φ-CH₂CH(CH₃)₂]⁺ | [B(C₆F₅)₄]⁻ |
| [(C₈H₁₇)—O-Φ-I-Φ]⁺ [B(C₆F₅)₄]⁻ | [C₁₂H₂₅-Φ-I-Φ-CH(CH₃)₂]⁺ [B(C₆F₅)₄]⁻ |
| [(C₈H₁₇—O-Φ)₂I]⁺ [B(C₆F₅)₄]⁻ | [CH₃-Φ-I-Φ-CH(CH₃)₂]⁺ [B(C₆F₅)₄]⁻ |
| [(C₈H₁₇)—O-Φ-I-Φ]⁺ [B(C₆F₅)₄]⁻ | [(Φ)₃S]⁺ [B(C₆F₅)₄]⁻ |
| [(Φ)₂S-Φ-O—C₈H₁₇]⁺ [B(C₆H₄CF₃)₄]⁻ | [(C₁₂H₂₅-Φ)₂I]⁺ [B(C₆F₅)₄]⁻ |
| [(Φ)₃S]⁺ [B(C₆F₄OCF₃)₄]⁻ and [(Φ-CH₃)₂ I]⁺, [B(C₆F₄OCF₃)₄]⁻. | [(Φ-CH₃)₂I]⁺ [B(C₆F₅)₄]⁻ |

8. A dental prostheses comprising the dental composition of claim 1, wherein the composition is polymerized and/or crosslinked.

9. A dental restoration comprising the dental composition of claim 1, wherein the composition is polymerized and/or crosslinked.

10. A dental prosthesis, comprising the dental composition of claim 2.

11. A dental restoration material, comprising the composition of claim 2.

12. The dental composition as claimed in claim 2 wherein the anionic entity of the initiator is a borate of formula [BX$_a$R$_b$]⁻ in which:
  a and b are integers ranging, for a, from 0 to 3 and, for b, from 1 to 4, with a+b=4,
  the symbols X represent:
    a chlorine atom or a fluorine atom with a=0 to 3, or
    an OH functional group with a=0 to 2,
  the symbols R are identical or different and represent:
    a phenyl radical substituted by at least one electron-withdrawing group, OCF₃, CF₃, NO₂ or CN, and/or by at least 2 halogen atoms, when the cationic entity is an onium of an element from Groups 15 to 17,
    a phenyl radical substituted by at least one electron-withdrawing element or group, CF₃, OCF₃, NO₂ or CN, when the cationic entity is an organometallic complex of an element from Groups 4 to 10,
    an aryl radical comprising at least two aromatic nuclei, which is optionally substituted by at least one electron-withdrawing element or group, OCF₃, CF₃, NO₂ or CN, whatever the cationic entity.

13. The composition as claimed in claim 2, wherein Z is an organic substituent Z1 comprising at least one epoxy and/or dioxolane reactive functional group and optionally at least one epoxy reactive functional group.

14. The composition as claimed in claim 2, wherein the oligomer or polymer (1) additionally comprises other reactive functional groups Z such as the alkenyl ether, oxetane and/or carbonate reactive functional groups Z2.

15. The composition as claimed in claim 2, wherein the reactive functional group or groups of Z1 are selected from the following radicals:

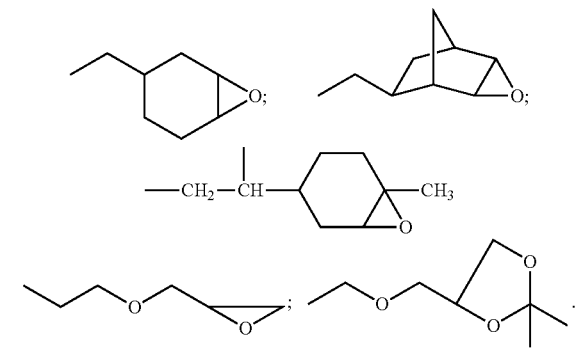

16. The composition as claimed in claim 2, wherein the photoinitiator is selected from the group consisting of:

| | |
|---|---|
| [CH₃-Φ-I-Φ-CH₂CH(CH₃)₂]⁺ | [B(C₆F₅)₄]⁻ |
| [(C₈H₁₇)—O-Φ-I-Φ]⁺ [B(C₆F₅)₄]⁻ | [C₁₂H₂₅-Φ-I-Φ-CH(CH₃)₂]⁺ [B(C₆F₅)₄]⁻ |
| [(C₈H₁₇—O-Φ)₂I]⁺ [B(C₆F₅)₄]⁻ | [CH₃-Φ-I-Φ-CH(CH₃)₂]⁺ [B(C₆F₅)₄]⁻ |
| [(C₈H₁₇)—O-Φ-I-Φ]⁺ [B(C₆F₅)₄]⁻ | [(Φ)₃S]⁺ [B(C₆F₅)₄]⁻ |
| [(Φ)₂S-Φ-O—C₈H₁₇]⁺ [B(C₆H₄CF₃)₄]⁻ | [(C₁₂H₂₅-Φ)₂I]⁺ [B(C₆F₅)₄]⁻ |
| [(Φ)₃S]⁺ [B(C₆F₄OCF₃)₄]⁻ and [(Φ-CH₃)₂ I]⁺, [B(C₆F₄OCF₃)₄]⁻. | [(Φ-CH₃)₂I]⁺ [B(C₆F₅)₄]⁻ |

17. The composition of claim 1, wherein said composition, after crosslinking/polymerization, has a Vicker's hardness of at least 30 for a load of 500 grams and has increased resistance to saliva abrasion.

18. The composition of claim 1, wherein said composition, after crosslinking/polymerization, has a Vicker's hardness of at least 40 for a load of 500 grams and has increased resistance to saliva abrasion.

19. The composition of claim 2, wherein said composition, after crosslinking/polymerization, has a Vicker's hardness of at least 30 for a load of 500 grams and has increased resistance to saliva abrasion.

20. The composition of claim 2, wherein said composition, after crosslinking/polymerization, has a Vicker's hardness of at least 40 for a load of 500 grams and has increased resistance to saliva abrasion.

21. A dental composition comprising:
  (A) a concentrated silica solution comprising 15 to 80% of colloidal particles of amorphous silica in at least one continuous silicone phase, wherein the at least one continuous silicone phase comprises a crosslinkable and/or polymerizable silicone oligomer and/or polymer which is liquid at ambient temperature or heat-fusible at a temperature below 100° C., the silicone oligomer and/or polymer comprising:
  (i) at least one unit of formula (FS):

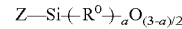

in which:
  a=0,1 to 2,
  R⁰, which are identical or different, represent an alkyl, cycloalkyl, aryl, vinyl, hydrogen, hydroxyl or alkoxy radical,
  Z, which are identical or different, is an organic substituent comprising at least one epoxy and/or alkenyl ether and/or oxetane and/or dioxolane and/or carbonate reactive functional group,
  (ii) and at least two silicon atoms, (B) at least one aromatic hydrocarbonaceous photosensitizer comprising one or more substituted or unsubstituted aromatic rings having a residual absorption of the light between 200 and 500 nm,
(C) at least one cationic initiator selected from those for which the cationic entity is selected from the onium salts of formula (I):

  (I)

in which formula:
A represents an element from Groups 15 to 17,
$R^1$ represents a $C_6$-$C_{20}$ carbocyclic or heterocyclic aryl radical, where the heteroelements in said heterocyclic aryl radical are nitrogen or sulfur,
$R^2$ represents $R^1$ or a linear or branched $C_1$-$C_{30}$ alkyl or alkenyl radical; said $R^1$ and $R^2$ radicals optionally being substituted by a $C_1$-$C_{25}$ alkoxy, $C_1$-$C_{25}$ alkyl, nitro, chloro, bromo, cyano, carboxyl, ester or mercapto group, n is an integer ranging from 1 to v+1, v being the valency of the element A,
m is an integer ranging from 0 to v−1 with n+m=v+1,
where the concentrated silica solution is prepared by:
(i) mixing a silica organosol with said silicone oligomer and/or polymer, where the organosol is selected such that its solvent is compatible with said silcone,
(ii) removing the solvent and
(iii) obtaining a concentrated silica solution as a dispersion of amorphous silica in a continuous silicone phase.

22. The composition of claim 1, wherein upon crosslinking, said composition is crosslinked to a greater distance than a similar composition in which the silica is present but was not included in the composition in a concentrated silica solution comprising 15 to 80% of colloidal particles of amorphous silica in at least one continuous silicone phase.

* * * * *